United States Patent [19]

Imran

[11] Patent Number: 4,768,512

[45] Date of Patent: Sep. 6, 1988

[54] CARDIOVERTING SYSTEM AND METHOD WITH HIGH-FREQUENCY PULSE DELIVERY

[75] Inventor: Mir Imran, San Francisco, Calif.

[73] Assignee: Mieczyslaw Mirowski, Owings Mills, Md.

[21] Appl. No.: 862,784

[22] Filed: May 13, 1986

[51] Int. Cl.$^4$ ............................................... A61N 1/36
[52] U.S. Cl. .................................................. 128/419 D
[58] Field of Search ........... 128/419 D, 419 R, 419 S, 128/419 PG, 421, 423 R

[56] References Cited

U.S. PATENT DOCUMENTS 3,614,955 10/1971 Mirowski et al. ............... 128/419 D
4,222,386 9/1980 Smolnikov et al. .......... 128/419 PG Primary Examiner—William E. Kamm
Attorney, Agent, or Firm—Fleit, Jacobson, Cohn & Price

[57] ABSTRACT

An implantable cardioverting system wherein a cardioverting or defibrillating voltage is automatically applied across implantable electrodes associated with the heart of a patient. The cardioverting voltage is an exponentially-decaying voltage pulse that is chopped, or broken, at high frequencies to provide a voltage wave packet formed of a plurality of high-frequency cardioverting pulses. The voltage is provided by an internal storage capacitor coupled across implantable electrode leads that is charged to a predetermined voltage level. Upon discharge, an electronic switch is clocked at frequencies preferably in excess of 1 KHz to open and close the circuit formed of the storage capacitor and electrodes.

10 Claims, 1 Drawing Sheet

CARDIOVERTING SYSTEM AND METHOD WITH HIGH-FREQUENCY PULSE DELIVERY

BACKGROUND OF THE INVENTION

The present invention relates to an implantable cardioverter or defibrillator system wherein a high-energy pulse is delivered to the heart of a patient. The high-energy pulse is chopped at a high frequency so that the pulse comprises a wave packet formed of a plurality of high-frequency cardioverting pulses.

In recent years, substantial progress has been made in the development of cardioverting techniques for effectively cardioverting, including defibrillating, various heart disorders and arrhythmias. Past efforts have resulted in the development of implantable electronic defibrillators which, in response to the detection of an abnormal cardiac rhythm, discharge sufficient energy via electrodes connected to the heart to depolarize and restore it to normal cardiac rhythm.

"Cardioverting" or "cardioversion" as used herein is intended to encompass the correction of a number of arrhythmic heart conditions, both lethal and non-lethal. These arrhythmic heart conditions include atrial tachycardia, atrial flutter, atrial fibrillation, junctional rhythms, ventricular tachycardia, ventricular flutter, ventricular fibrillation, and any other non-pacemaking related arrhythmic conditions which may be corrected by applying electrical shocks to the heart. The term "defibrillation" is included in the term cardioversion as a method of applying electrical shocks to the heart to defibrillate fibrillating atria or fibrillating ventricles.

Prior art implantable cardioverting systems typically include the detection of an arrhythmia condition which in turn initiates the charging of a storage capacitor by a high-voltage inverter circuit (or DC-to-DC converter circuit). See, for example, U.S. Pat. No. 4,164,946, assigned to the present assignee. Following the charging of the storage capacitor, and upon determination that a cardioverting or defibrillating shock is to be issued to the heart of the patient via implantable electrodes, the capacitor is coupled across the implantable electrodes and the capacitor voltage is applied thereto. The capacitor discharge provides a single high-voltage pulse, in the form of an exponentially-decaying waveform, across the electrodes, and through the heart tissue, to depolarize the heart.

The delivered high-energy pulse in such cardioversion systems is a single DC pulse and thus the impedance of the heart is substantially a function of the DC impedance component, or resistance, of the heart. The impedance of the heart in response to a single DC voltage pulse applied thereto is relatively low and uniform and thus the pulse is not optimally dispersed throughout the heart, but rather to a relatively localized area of the heart. As a result, in order to depolarize a greater area of the heart, without altering the electrode geometry, higher energies must be employed, which have inherent limits in implantable devices.

SUMMARY OF THE INVENTION

The present invention relates to a cardioversion system that chops, or breaks, the exponentially-decaying waveform provided across the implantable electrodes at a high frequency, preferably greater than 1 KHz. An electronic switch is provided in series between the storage capacitor and the implantable electrodes and a clocking signal is provided to the switch to open and close the switch at a high frequency. As a result, the pulse provided to the heart comprises a single wave packet formed of a plurality of high-frequency cardioverting pulses.

The present invention recognizes that the impedance of the heart tissue (created by the myocardium, fat, and blood) changes at different frequencies. At high frequencies, the impedances of different components of the heart tissue are different, with areas of high impedance and areas of low impedance being dispersed throughout the heart. As a result, by pulsing the heart with high-frequency pulses, the energy is distributed throughout the heart thus resulting in lower energy requirements for effective cardioversion.

Thus, it is an object of the present invention to provide a cardioverting system that detects arrhythmias and cardioverts the heart of a patient by delivering a wave packet formed of a plurality of high-frequency pulses across the implantable electrodes.

It is further an object of the present invention to provide high-frequency pulses to the heart of a patient by chopping the exponentially decaying waveform at a high frequency. The chopping is provided by an electronic switch that is broken at a high frequency, preferably greater than 1 KHz.

These and other objects of the invention will be apparent when reference is made to the foregoing description.

DETAILED DESCRIPTION OF THE PREFERRED EMBODIMENT

Figure 1:
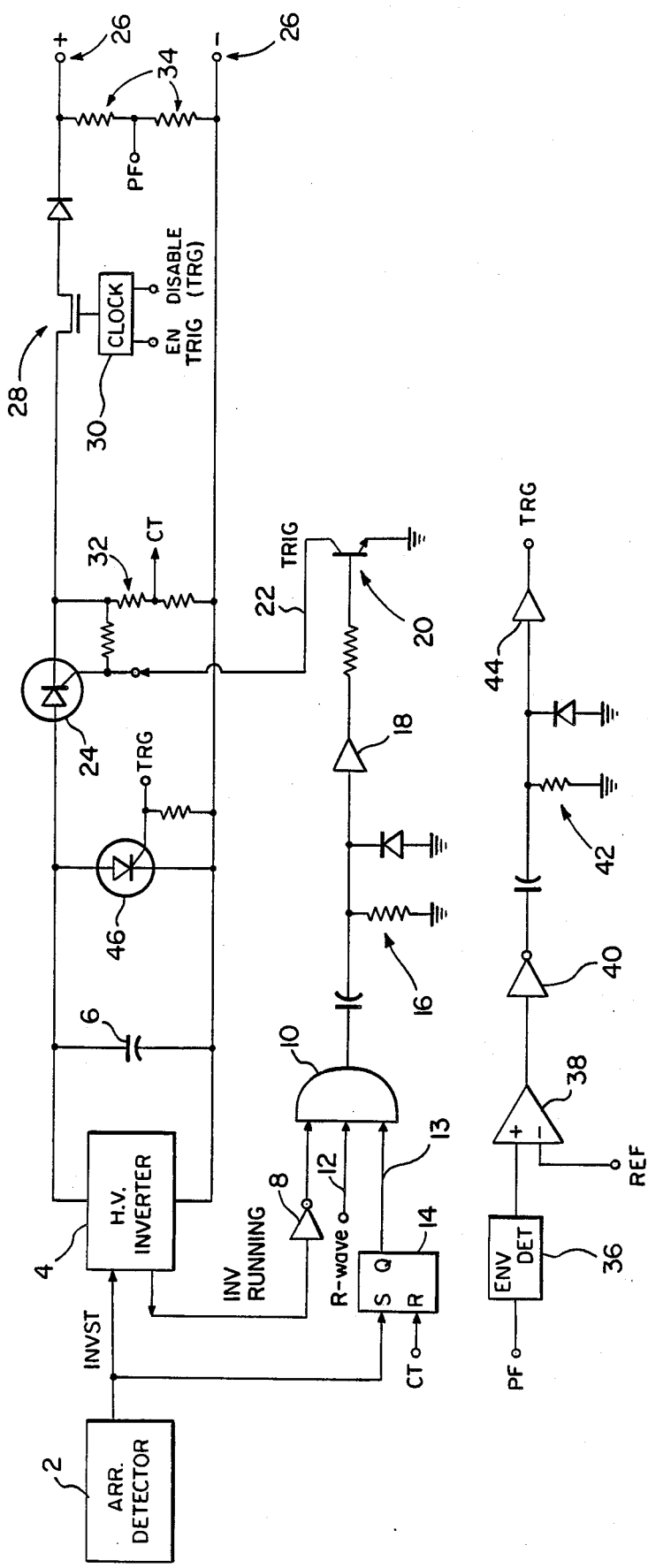
FIG. 1 is a schematic diagram of the cardioverting system of the present invention.

The cardioverting system of the present invention is depicted schematically in FIG. 1. The system includes a number of circuit elements common to copending U.S. patent application Ser. No. 478,038 to Imram et al, filed on Mar. 23, 1983, and assigned to the same assignee as the instant application, now U.S. Pat. No. 4,614,192. The Imran et al application is incorporated herein by reference.

An arrhythmia detector circuit 2 is coupled with implantable electrodes (not shown) that are, in turn, connected with the heart of a patient. The arrhythmia detector circuit 2 is capable of detecting an arrhythmic condition and providing an INVST output signal thereupon. The arrhythmia detecting circuit 2 may include a heart rate detector circuit and a probability density function (PDF) circuit such that when the heart rate exceeds a predetermined threshold, and the probability density function conditions are satisfied, the INVST signal is issued to a high-voltage inverter and control circuit 4. The rate analysis and PDF circuits are described in the copending Imran et al application. It should be apparent that other schemes for detecting an arrhythmia may be employed to provide a start signal (or INVST signal) to a high-voltage inverter circuit 4.

The high-voltage inverter 4, also known as a DC-to-DC converter, is a conventional element well known in the implantable defibrillator art. Reference should be made, for example, to U.S. Pat. No. 4,164,946, which describes the DC-to-DC converter (element 30 in U.S. Pat. No. 4,164,946). Upon receipt of the INVST signal, the high-voltage inverter 4 charges an internal energy storage capacitor 6 which is charged to a predetermined level. When the high-voltage inverter 4 begins operation upon receipt of the INVST signal, the high-voltage inverter begins running, or charging, the capacitor 6, and provides an INV RUNNING signal through inverter logic element 8, which is connected to an input of AND gate 10.

The AND gate 10 has two additional inputs. Input 12 is from an R-wave detector as disclosed in the copending Imran et al application. Upon detection of each R-wave, a signal is provided to input 12 of the AND gate 10. Input 13 of the AND gate 10 is from flip-flop 14, which is set upon receipt of the INVST signal from the arrhythmia detector 2. The flip-flop 14 is reset upon receipt of a CT signal, to be described below.

Upon the detection of an arrhythmic condition and the issuance of an INVST signal, the high-voltage inverter starts running and issues an INV RUNNING signal which is inverted by inverter logic element 8 to provide a low input to the AND gate 10. When the inverter stops running, i.e., at the completion of the charging of the storage capacitor 6, the output of inverter logic element 8 goes high. A subsequent R-wave input to the AND gate 10 causes a pulse to be emitted, through a suitable RC pulse-shaping network 16 and buffer 18 to a transistor 20. The transistor 20 is then actuated and a patient trigger pulse (TRIG) is applied over lead 22 to fire a patient SCR 24. Upon the firing of patient SCR 24, the fully charged capacitor 6 is then capable of discharging across leads 26 which are connected to the electrodes (not shown) associated with the heart of a patient.

Connected in series between the capacitor 6 and the electrode lead terminals 26 is a power field effect transistor (FET) 28. The power FET 28 is coupled with a clock pulse generator 30 which provides high-frequency clocking pules to the gate of the FET 28. The clocking pulses are provided to the FET 28 upon receipt of a TRIG signal when the transistor 20 is turned on.

The clocking pulses from the clock pulse generator 30 serve to turn the power FET on and off at a high frequency, in accordnace with the frequency of the clocking pulse generator 30. Preferably, the clock pulse generator 30 provides actuating pulses to the FET 28 at a frequency at least equal to 1 KHz and preferably between 10 KHz and 1 MHz.

Thus, the TRIG pulse from transistor 20 turns on SCR 24 and enables the clock pulse generator 30. The capacitor 6 then discharges across the electrode leads 26, at a frequency proportional to the clock pulse frequency from the clock pulse generator 30. A pair of resistors 32 connected in parallel with the terminals 26 detects the discharge via the CT lead. This CT lead is connected to the reset terminal of flip-flop 14 and, upon detection of the discharge, a CT pulse resets the flip-flop.

Also connected in parallel across the electrode leads 26 are a pair of resistors 34 which detect the pulse discharge applied across the electrode leads 26. This pulse feedback signal (PF signal) is provided to an envelope detector 36. The envelope detector 36 detects the envelope of the high-frequency exponentially decaying pulses and provides the detected envelope signal to a positive input terminal of a comparator 38. The comparator 38 has a negative terminal coupled to a reference voltage. When the voltage of the detected envelope drops below the reference, the comparator 38 provides an output which is inverted by inverter 40, shaped by pulse-shaping network 42, through a buffer 44, to provide a TRG signal. The TRG signal is provided to a disable terminal of the clock pulse generator 30 to stop the clock pulse generator from delivering further clock pulses to the FET 28. The TRG signal is also provided to a truncate SCR 46 to fire the truncate SCR 46. When the truncate SCR 46 is fired, the exponentially decaying pulse across the electrode terminals 26 is truncated or shorted so that no further energy is delivered to the electrodes. This is done since it is undesirable to require the pulse to exponentially decay to a zero level, as was stated in the copending Imran et al application.

In operation, detection of an arrhythmic condition by the arrhythmia detector 2 initiates the running of the high-voltage inverter circuit 4. When the inverter circuit completes its charging of the capacitor 6, and, upon receipt of an R-wave via lead 12, the AND gate 10 is asserted and a trigger pulse (TRIG pulse) is issued by transistor 20 to fire the patient SCR 24 and to enable the clock pulse generator 30. The capacitor 6 then discharges across the electrode lead terminals 26 and the exponentially decaying wave form is chopped by the high-frequency actuation of the power FET 28.

Figure 2:
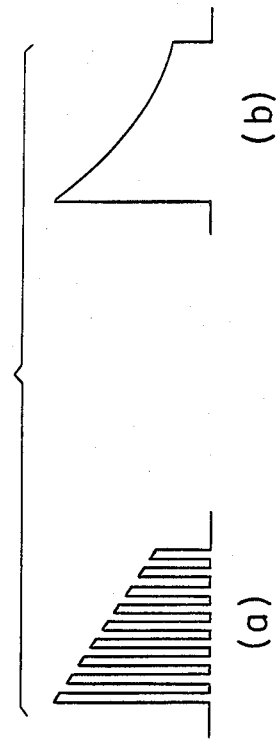
FIG. 2 depicts the exponentially decaying waveforms of the prior art and of the present invention.

Wave form (a) of FIG. 2 depicts the chopped exponentially decaying wave form in exaggerated form. In essence, the wave form (a) of FIG. 2 is a wave packet comprising a plurality of high-frequency cardioverting or defibrillating pulses that are applied across the electrode leads 26. Wave form (b) of FIG. 2 depicts an exponentially decaying wave form that is not chopped in accordance with the present invention and thus is similar to the type of pulse delivered in prior defibrillating systems.

Above, a preferred embodiment of the present invention is disclosed. It should be appreciated, however, that the present invention is not limited to the specific embodiment disclosed herein, but solely with reference to the following claims.

What is claimed is:

1. In a cardioversion system for automatically cardioverting the heart of a patient including a storage capacitor, a means for charging the storage capacitor to a predetermined voltage level, a means for discharging the storage capacitor, and a pair of implantable electrodes connectable with said storage capacitor whereby the discharge of the storage capacitor provides an exponentially decaying voltage across said electrodes, wherein the improvement comprises:
    chopping means for electrically connecting said storage capacitor with said implantable electrodes at a predetermined frequency for chopping the exponentially decaying voltage across said implantable electrodes.

2. The cardioversion system as claimed in claim 1 wherein said chopping mean comprises an electronic switch connected in series between said storage capacitor and said implantable electrodes, and clocking means coupled with said electronic switch for opening and closing the electronic switch at a predetermined frequency.

3. The cardioversion system as claimed in claim 2 wherein said electronic swtich comprises a field effect transistor.

4. An implantable cardioversion system for automatically cardioverting the heart of a patient, comprising:

detecting means for detecting arrhythmias of the heart;

cardioverting means responsive to said detecting means for delivering to the heart at least one wave packet of high-frequency cardioverting pulses.

5. The implantable cardioverter of claim 4 wherein said cardioverting means includes means for delivering high-frequency cardioverting pulses at a frequency between 10 KHz and 1 MHz.

6. The implantable cardioverter of claim 5 wherein said cardioverting means includes means for delivering high-frequency cardioverting pulses at a frequency between 10 KHz and 1 MHz.

7. A method of automatically cardioverting the heart of a patient through implantable electrodes comprising the steps of:

detecting an arrhythmic condition of the heart;

automatically cardioverting the heart in response to detecting the arrhythmia by delivering at least one cardioverting wave packet of high-frequency cardioverting pulses across the implantable electrodes.

8. The method of claim 7 wherein said delivering step comprising delivering an exponentially-decaying voltage wave packet of high-frequency cardioverting pulses.

9. The method of claim 7 wherein said cardioverting step comprises the steps of coupling a voltage of sufficient magnitude to depolarize the heart across the implantable electrodes and chopping the voltage at a predetermined frequency.

10. The method of claim 9 wherein said coupling step includes the step of coupling a charged capacitor across the implantable electrodes.

* * * * *